US008375805B2

(12) United States Patent
Prevey (10) Patent No.: US 8,375,805 B2
(45) Date of Patent: Feb. 19, 2013

(54) METHOD AND APPARATUS FOR SENSING DISTORTION

(75) Inventor: Paul S. Prevey, Cincinnati, OH (US)

(73) Assignee: Surface Technology Holdings, Ltd., Cincinatti, OH (US)

(*) Notice: Subject to any disclaimer, the term of this patent is extended or adjusted under 35 U.S.C. 154(b) by 231 days.

(21) Appl. No.: 12/387,259

(22) Filed: Apr. 30, 2009

(65) Prior Publication Data

US 2009/0211367 A1 Aug. 27, 2009

(51) Int. Cl.
*G01N 3/02* (2006.01)
*G01N 3/04* (2006.01)
*G01N 3/20* (2006.01)

(52) U.S. Cl. ............ 73/856; 73/849; 219/121.85
(58) Field of Classification Search ............ 702/81, 702/82; 219/121.82, 121.83, 121.85
See application file for complete search history.

(56) References Cited

U.S. PATENT DOCUMENTS

| | | | |
|---|---|---|---|
| 3,866,473 A | 2/1975 | Teitelbaum et al. | |
| 3,923,946 A | 12/1975 | Meyer | |
| 4,320,463 A * | 3/1982 | Himmelstein | 702/84 |
| 4,715,204 A | 12/1987 | Ottlik | |
| 4,796,900 A | 1/1989 | Gant et al. | |
| 4,806,778 A | 2/1989 | Yamamoto et al. | |
| 5,031,460 A | 7/1991 | Kanerobu et al. | |
| 5,199,304 A | 4/1993 | Ferguson | |
| 5,233,727 A * | 8/1993 | Baechler | 73/159 |
| 5,329,684 A | 7/1994 | Budet et al. | |
| 5,531,570 A * | 7/1996 | Mannava et al. | 416/241 R |
| 5,563,349 A | 10/1996 | Burke et al. | |
| 5,735,028 A | 4/1998 | Furusawa et al. | |
| 5,910,894 A * | 6/1999 | Pryor | 700/95 |
| 5,917,726 A * | 6/1999 | Pryor | 700/95 |
| 5,929,346 A | 7/1999 | Fukami | |
| 5,948,293 A * | 9/1999 | Somers et al. | 219/121.85 |
| 5,951,790 A * | 9/1999 | Mannava et al. | 148/510 |
| 6,089,101 A | 7/2000 | Ishii et al. | |
| 6,094,260 A * | 7/2000 | Rockstroh et al. | 356/35.5 |
| 6,148,676 A | 11/2000 | Bergs | |
| 6,914,215 B2 * | 7/2005 | Davis et al. | 219/121.85 |
| 6,969,821 B2 * | 11/2005 | Mika et al. | 219/121.83 |
| 2003/0009898 A1 | 1/2003 | Slocum et al. | |
| 2003/0173341 A1 * | 9/2003 | Matsushita | 219/121.83 |
| 2004/0139809 A1 | 7/2004 | Soechting et al. | |
| 2005/0068989 A1 | 3/2005 | Herbert et al. | |

OTHER PUBLICATIONS

David Hornbach and Paul Prevey, Development of Machining Procedured to Minimize Distortion During Manufacture, 1998, "Heat Treating" Procedures of the 17th Heat Treating Society Conference and Exposition, ASM, Metals Parks, OH, pp. 13-18.

* cited by examiner

*Primary Examiner* — Lisa Caputo
*Assistant Examiner* — Punam Roy
(74) *Attorney, Agent, or Firm* — Mark F. Smith; Smith Brandenburg Ltd.

(57) ABSTRACT

A work holder capable of measuring the amount of distortion occurring in a part as the part is machined, processed, treated, or otherwise operated upon and methods of using the same for quality control and process monitoring purposes. Indirect measurement of the distortion occurring in the part eliminates the need to individually strain gauge each part.

5 Claims, 6 Drawing Sheets

Flow chart of quality control procedure based on amount of distortion

Flow chart for real time evaluation and adjustment of treatment process

FIG. 3: Flow chart of quality control procedure based on distortion signature

FIG. 4: Flow chart of quality control procedure based on amount of distortion

FIG. 5: Flow chart for evaluating proper operation of treatment process

FIG. 6: Flow chart for real time evaluation and adjustment of treatment process

METHOD AND APPARATUS FOR SENSING DISTORTION

CROSS-REFERENCE TO PRIOR APPLICATION

This application is based on and claims benefit to U.S. patent application Ser. No. 11/152,612, filed on Jun. 14, 2005, which claims benefit to Provisional Patent Application Ser. No. 60/579,489, filed Jun. 14, 2004.

BACKGROUND OF THE INVENTION

This invention relates to an apparatus for securing a part, such as a work holder or fixture, capable of monitoring, sensing, or measuring the mechanical distortion of the part as it is machined, treated or otherwise operated on.

It is well known that metallic parts, such as aircraft engine parts, may distort when subjected to processes such as burnishing, shot peening, laser shock peening, or other similar treatments. These distortions are caused by compressive stresses that are introduced and tensile stresses that develop in the part as a result of such processes. A part may be subjected to processes such as burnishing, shot peening or laser shock peening to improve the parts resistance to stress related failure mechanisms. The benefit of such processes is obtained by inducing compressive stresses in the surface of the part. Metallic materials treated in such a manner respond to the introduction of compressive stresses by being self-equilibrating. Thus, as compressive stresses are introduced in the part, reacting tensile stresses form elsewhere in the part such that all forces within the volume of the part sum to zero. However, as these stresses develop, the material forming the part may react by distorting to accommodate the introduction of new stresses.

One problem associated with such distortions is that they go beyond the acceptable engineering tolerances for that particular part. While the mechanisms that cause distortion are known and understood, monitoring individual parts for excessive distortion beyond acceptable engineering tolerances has been difficult because of the various factors that contribute to distortion as well as the complexity of many part designs. Factors that have been found to contribute to distortion include the type, magnitude and pattern of stress introduced in the part, the particular method by which the part was treated, the material(s) from which the part is made, and the particular geometry of the part. Another substantial factor which impacts distortion are variations in individual parts, most notably in parts being treated that have already undergone some service life and are being remanufactured or refurbished. Under such circumstances, it becomes even more critical to monitor the response of each individual part to the treatment process for quality control purposes. Furthermore, for parts having complex geometries, such as gas turbine engine blades, it is difficult to measure the degree to which the part may have distorted, especially in the context of a sizeable manufacturing operation.

Accordingly, until now, it has been impractical or unduly laborious to measure individual parts and thereby assess whether a part has been adequately processed or whether a particular treatment operation has caused distortion beyond acceptable engineering tolerances. Therefore, a need exists for a relatively inexpensive method and apparatus for determining the distortion of a part as a result of a treatment process and that is easily implemented in a manufacturing environment.

SUMMARY OF THE INVENTION

The subject invention relates to a distortion sensing work holder for securing a part during a machining, treatment, or other process that is capable of monitoring, measuring, recording or otherwise sensing the mechanical distortion of the part as it is subjected to the process. The distortion sensing work holder is preferably capable of monitoring, sensing, or measuring the mechanical distortion of the part as it is machined, treated or otherwise operated upon.

By way of description, a preferred embodiment of the distortion sensing work holder would be used in the following manner: A part to be treated is clamped in a work holder. Once the part is clamped it is attached to a linkage such that the part is in mechanical communication with an elastically deformable element. The linkage may be attached to the part with bolts, clamps, and the like, or specially designed grippers wherein the gripping faces of the gripper correspond to the contours of the specific part. With the part secured and in mechanical communication with the elastically deformable element, the part is treated by burnishing, laser shock peening or other similar surface treatments. As the part is treated, distortions in the part that may result from the treatment process are communicated, via the linkage, to the elastically deformable and recoverable element. Strain sensors or deflection sensors mounted on the deformable element sense the distortion and output a signal corresponding to the magnitude of the distortion. This signal is recorded throughout the treatment process. Based on this signal, a distortion signature indicative of the distortions experienced by the part over the course of the treatment procedure is compiled for that particular process and part combination. This signature may then be utilized for quality control and process evaluation purposes for subsequent treatment procedures.

In another preferred embodiment of the invention, the distortion sensing work holder provides a means for monitoring the repeatability of machining, treating, or other procedures as a measure of quality control.

In another preferred embodiment of the invention, the distortion sensing work holder is effective for providing a means to monitor a machining, treating, or other process to ensure proper operating conditions for the process.

In another preferred embodiment of the invention, the distortion sensing work holder is effective for providing means for monitoring the progress of a machining, treating, or other process and to provide corrective action when the process deviates from acceptable or established parameters.

In another preferred embodiment of the invention, the distortion sensing work holder is effective for providing an apparatus for securing a part during a machining, treatment, or other process that is capable of monitoring, measuring, recording, or otherwise sensing the distortion of a part as it is subjected to the process, utilizing the output of such an apparatus to develop a distortion signature for the particular process; and utilizing the distortion signature to monitor the process for abnormal operating conditions; and utilizing the distortion signature as a quality control measure for individual parts.

In another preferred embodiment of the invention, the distortion sensing work holder comprises a means for securing a part being treated; a rigid, elastically deformable and recoverable material fixedly attached to the securing means; a means for mechanically linking the part being operated upon to the rigid, elastically deformable and recoverable material; a means for measuring the strain developed in or the deflection of the material; and a means for capturing and recording the output of the strain or deflection measuring means.

In another preferred embodiment of the present invention, the distortion sensing work holder comprises a means for clamping a part, the clamping means having a base integrally formed with a support member for supporting the base on a conventional tool holder; a rigid, elastically deformable and recoverable material in the shape of a beam, the beam having a first and second end, the second end being fixedly attached to the base of the clamping means; strain or deflection sensing means fixedly attached between the first and second ends of the beam and between the beam and the base of the clamping means; a linkage for communicating distortions from a part to the beam, the linkage having top and bottom ends, the bottom end of the linkage being fixedly attached to the first end of the beam, the top end of the linkage having means for gripping and releasing the end of a part opposite the means for clamping; a means for monitoring, recording over time, and analyzing the output of the strain or deflection sensing means, the means for monitoring, recording, and analyzing having a human readable display of the information collected.

In another preferred embodiment of the invention, the distortion sensing work holder comprises a means for securing a part being treated; a means for measuring the deflection of the part being treated; and a means for capturing and recording the output of the deflection measuring means.

In another preferred embodiment of the present invention, the distortion sensing work holder comprises a means for clamping a part, the clamping means having a base integrally formed with a support member for supporting the base on a conventional tool holder; selectively positionable deflection measuring means; and a means for monitoring, recording, and analyzing the output of the deflection sensing means, the means for monitoring, recording, and analyzing having a human readable display of the information collected.

Another preferred embodiment of the invention is a method for using a distortion sensing work holder for quality control purposes. The method comprises the steps of placing a part to be machined, treated or otherwise operated upon in the distortion sensing work holder; obtaining a distortion signature for the particular operation by recording the output of the strain or deflection sensing means as a function of time or the position of the tooling during treatment; comparing the recorded distortion signature against a known or verified signature for the same operation on the same part; determining if the part is acceptable based upon the comparison between the known signature and the recorded signature.

In another preferred embodiment of the present invention, the apparatus is used in conjunction with a method for determining abnormal operation of the equipment operating on the part. The method comprises placing a part to be machined, treated or otherwise operated upon in the distortion sensing work holder; obtaining a distortion signature for the particular operation by recording the output of the strain or deflection sensing means; comparing the recorded distortion signature against a known or verified signature for the same operation on the same part; determining if the part is acceptable based upon the comparison between the known signature and the recorded signature.

The method and apparatus of the present invention can be used to measure the distortion occurring in parts with a high length to cross-sectional area ratio including, but not limited to, turbine and compressor blades, turbine and compressor vanes, stator vanes, inlet guide vanes, impellers, propellers, propulsers, aircraft skin materials, medical implant devices, and other various and sundry applications too numerous to mention herein.

Other embodiments and advantages of the invention will be apparent from the following description, the accompanying drawings and the appended claims. While the methods and apparatus described constitutes preferred embodiments of the invention, it is to be understood that the invention is not limited to the precise method and apparatus, and that changes may be made therein without departing from the scope of the invention which is defined in the appended claims.

BRIEF DESCRIPTION OF THE DRAWINGS

To provide a more complete understanding of the present invention and further features and advantages thereof, reference is now made to the following description taken in conjunction with the accompanying drawings, in which.

DETAILED DESCRIPTION OF THE PREFERRED EMBODIMENT OF THE INVENTION

Although the foregoing invention has been described in some detail for purposes of clarity of understandings, it will be apparent that certain changes and modifications may be practiced within the scope of the appended claims. Accordingly, it should be understood that the present disclosure is to be considered as exemplary of the principals of the invention and is not intended to limit the invention to the embodiments and the specific examples illustrated and the invention is not to be limited to the details given herein, but may be modified within the scope and equivalents of the descriptions and examples contained herein.

Figure 1:
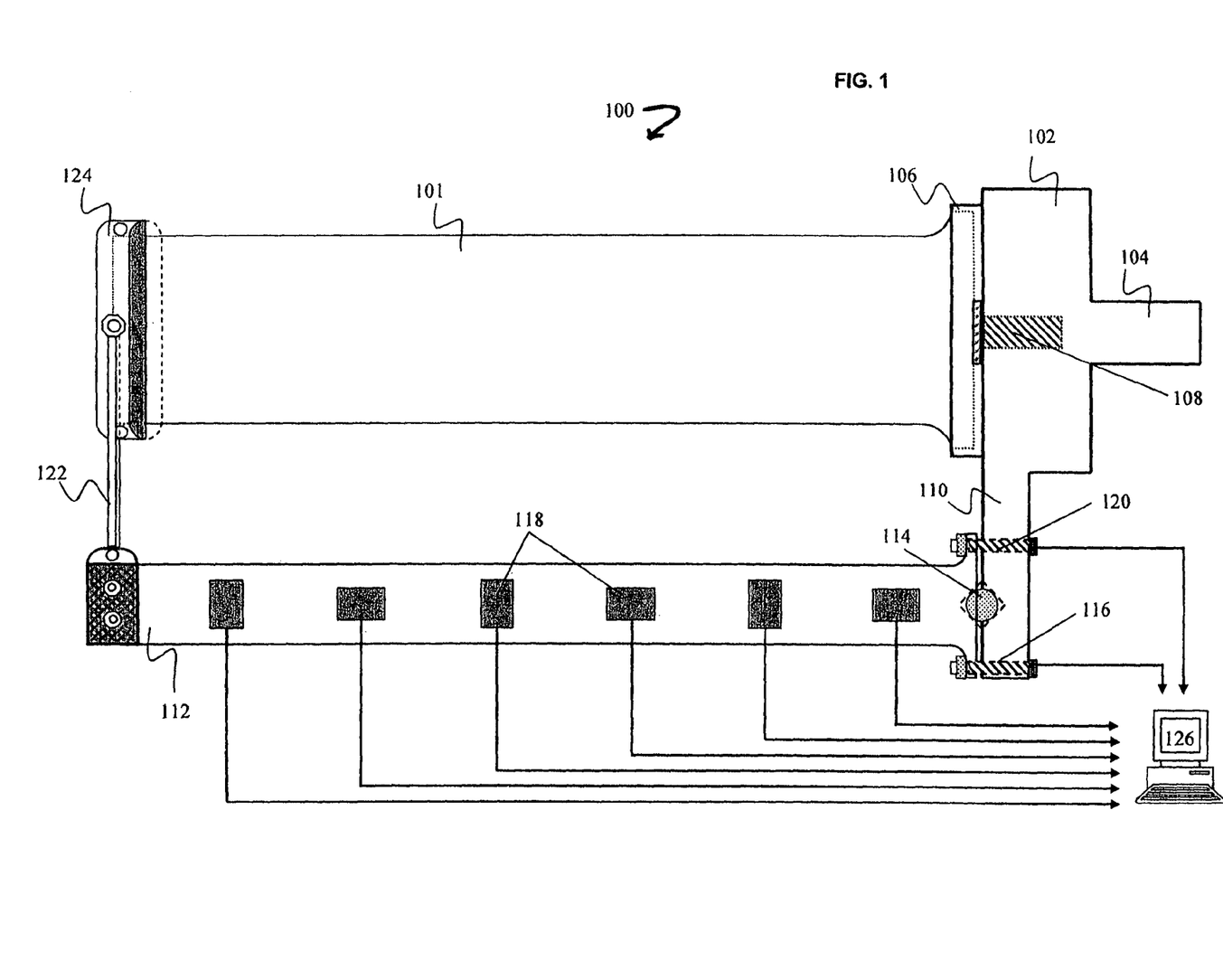
FIG. 1 is a schematic illustration of a preferred embodiment of the distortion sensing work holder that is the subject of the current invention.

Referring to FIG. 1, the work holder 100 for measuring the distortion of a part 101 is shown. For illustration purposes the part 101 shown is a blading member of a gas turbine engine. Preferably, work holder 100 comprises a base 102 integrally formed with an extension 110 and a support member 104. The support member 104 is standardized such that the work holder 100 may be secured in the tool holder of a conventional machine tool (not shown). A securing means 106 is rotatably attached to the base 102 via the spindle 108. The securing means 106 is interchangeable and may include vices, clamps, collets, slotted connectors, and other such means, and is selected based on the geometry of the part being operated on. In the embodiment described herein, the securing means 106 is a dovetail slot. The spindle 108 permits the securing means 106 to be rotated relative to the base thereby allowing flexibility in the orientation of the part being operated upon.

An elastically deformable and recoverable material member 112, which may be formed from metal, polymers, composites, or a combination of such materials, and in the form of a beam, rod, plate, and the like, is preferably flanged at one end, is attached to the extension 110 by fasteners 116 and 120, preferably instrumented bolts. Interposed between the extension 110 and the elastically deformable and recoverable member 112 is a spherical pivot point 114 that permits the deflection of the elastically deformable and recoverable member 112 in any direction relative to the base 102. Strain or deflection sensing means 118, preferably inductive sensors, capacitive sensors, lasers, ultrasonic sensors, mechanical sensors, transducers including LVDT displacement transducers and non-contact displacement transducers, strain gauges, air aes, instrumented bolts, instrumented washers, electro-optical devices, load cells, and other like means, are attached in various orientations along the length of the elastically deformable and recoverable member 112. A linkage 122 is fixedly attached to the distal end of the elastically deformable and recoverable material member 112. The linkage extends upward and terminates in a gripping element 124 having opposed gripping faces capable of firmly adhering to the unique contours of the part being operated upon. Preferably, the gripping faces are adjustable and correspond to the specific geometry of the portion of the part with which they contact. Finally, the output of the instrumented bolts 116, 120 and the strain or deflection sensing means 118 is fed to means for capturing, and recording the output of the strain or deflection measuring means. Such means 126 include computers, strip chart recorders, multi-meters, and other similar means. Preferably, means 126 comprises a computer controlled monitoring system capable of collecting, recording, and analyzing the respective output signals.

By way of setup, the part 101, in this example a turbine blade with a dovetail connector, is placed in the work holder 100 by first inserting the dovetail connector into the dovetail slot of the securing means 106. The securing means 106 is then rotated to present the proper profile of the part 101 to the operating tool (not shown). With the part 101 oriented and clamped in place, the linkage 122 is positioned such that the gripping element 124 contacts the surface of the part 101 on the end opposite the securing means 106. The gripping element 124 is then adjusted so that it firmly grips the edge of the part 101. As a treatment operation is performed on the part 101, any distortions developed in the part 101 are communicated to the elastically deformable and recoverable beam 112 via the linkage 122. Any distortion of the member 112 is registered by the strain or deflection sensing means 118 and/or the instrumented fasteners 116 and 120 and recorded by the monitoring system 126.

Figure 2:
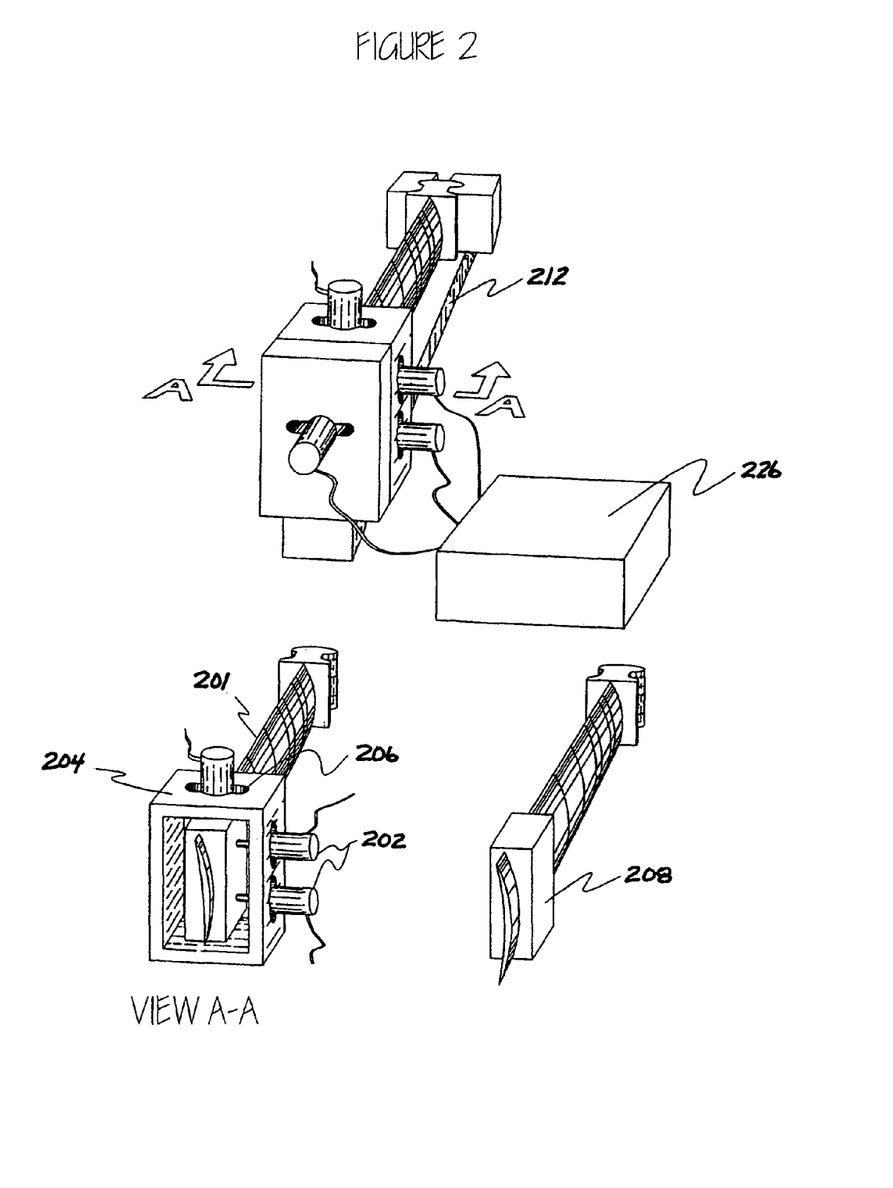
FIG. 2 is a schematic illustration of another preferred embodiment of the distortion sensing work holder that is the subject of the current invention.

Referring to FIG. 2, another embodiment of the distortion sensing work holder is shown. In this embodiment, the work holder has a plurality of proximity sensors 202 attached to positioning bracket 204 which, in turn, is attached to the distal end of the member 212 and adjustably arrayed around the part to be treated 201. The proximity sensors 202 are selected from the list including, but not limited to, capacitive sensors, inductive sensors, lasers, ultrasonic sensors, mechanical sensors, LVDT displacement transducers, non-contact displacement transducers, strain gauges, or air gauge sensors. The positioning bracket 204 employs means 206 for precisely positioning the sensors 202 relative to the part to be treated 201. The positioning means 206 may be selected from the various know means, such as digital micrometers, barrel micrometers, and the like. The proximity sensors 202 are positioned around the part to be treated so as to be able to measure the parts position in the x, y, and z directions. A sleeve 208 is placed around the distal end of the part 201 to provide a uniform registration surface for interfacing the proximity sensors 202 with the part 201. The output of the proximity sensors 202 is fed to a computer controlled monitoring system 226 capable of collecting and analyzing the respective output signals.

By way of operation, any distortions in the part being treated 201 will cause the part to deflect relative to the proximity sensors 202 which, in turn, output a signal corresponding to the magnitude and direction of the deflection in each of the x, y, and z directions. These signals are passed to the monitoring system 226 that records the output of the proximity sensors before, after, and throughout the treatment operation.

Figure 3:
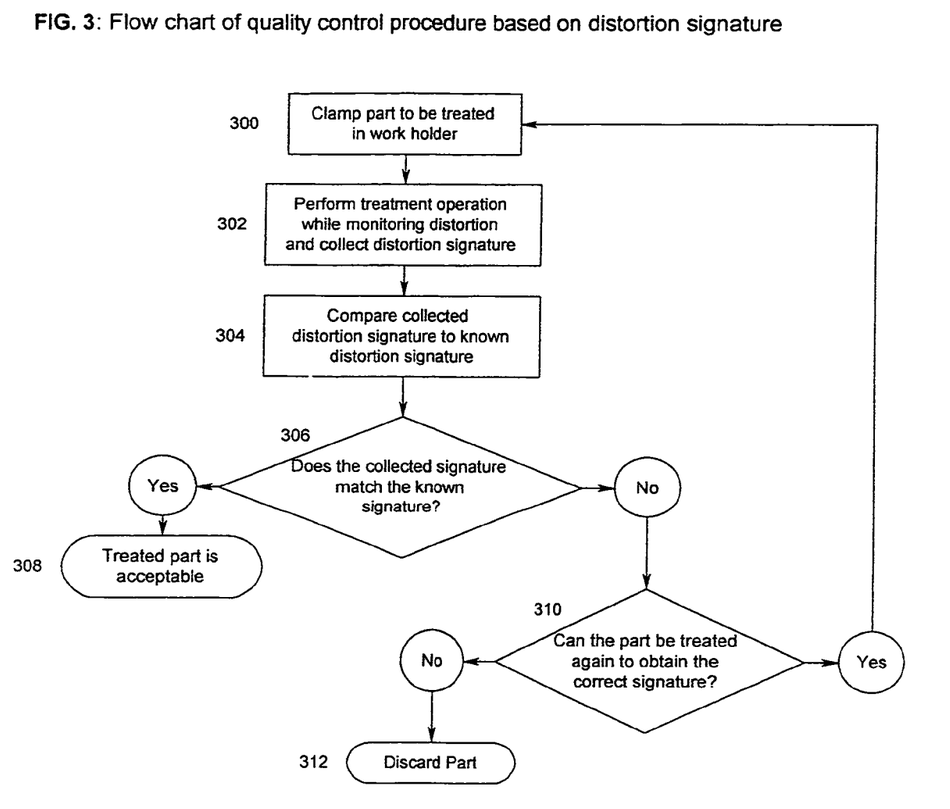
FIG. 3 is a flow diagram of a quality control procedure utilizing a distortion signature.

Referring now to the flow diagrams of FIGS. 3-6, several different methods of using the apparatus of the current invention for quality control and process monitoring are disclosed. Referring to FIG. 3, in one preferred embodiment, the work holder of the present invention is used for quality control purposes. In step 300, a part is clamped in the work holder and operated on while a real time distortion signature is collected as indicated in step 302. Thereafter, in step 304, the collected signature is compared to a known signature for a successful treatment operation. Step 306 consists of a decision point in which the success of the operation is determined. If there is agreement between the collected and known signatures, the treatment operation has been successful. If there is no agreement between the known and collected signatures, then the process proceeds to step 310 where the collected signature is analyzed to determine if an appropriate level of agreement could be reached by further processing. The process is either repeated to obtain the correct distortion or the part is otherwise discarded as indicated in step 312.

Figure 4:
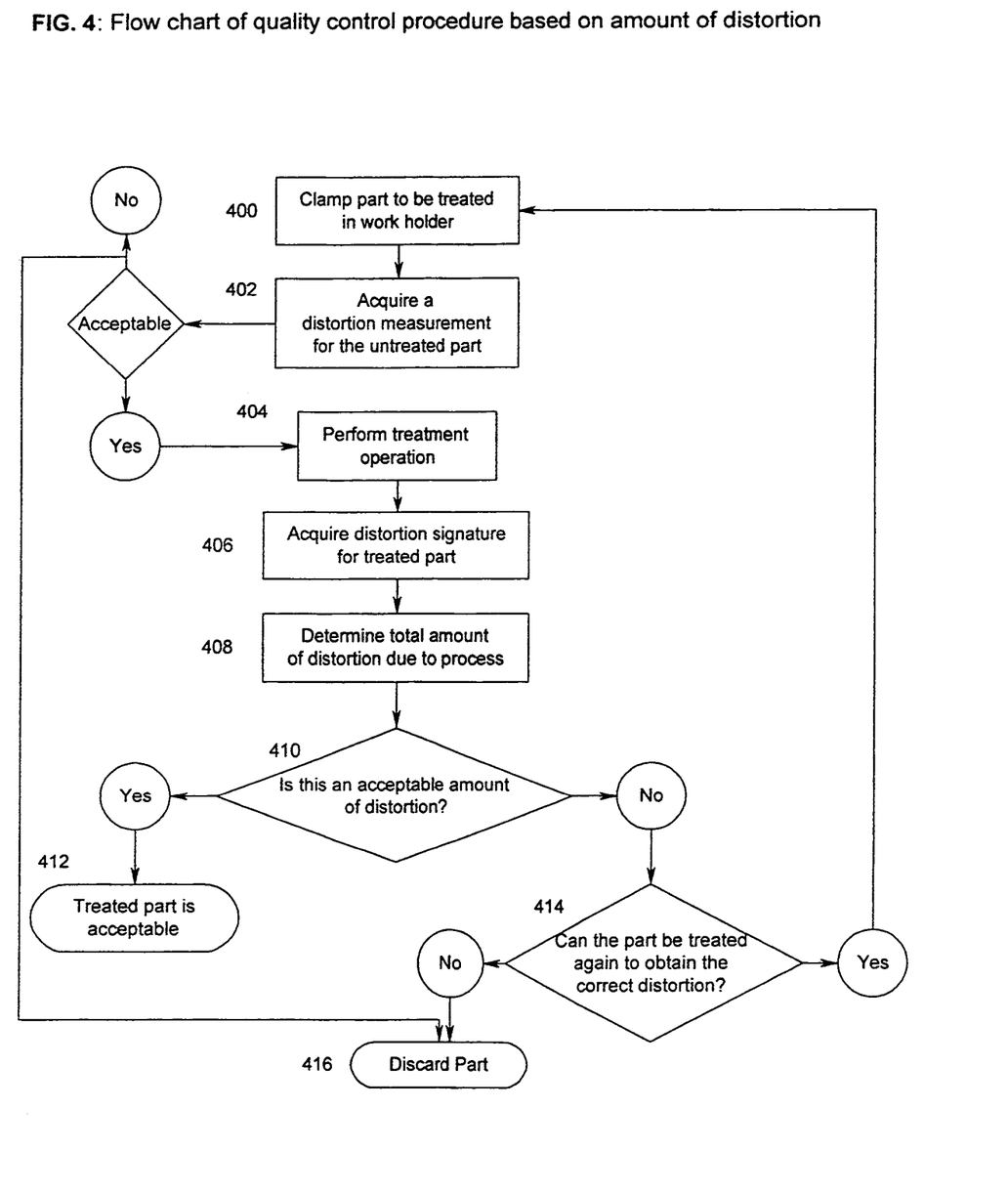
FIG. 4 is a flow diagram of a quality control procedure based on the amount of distortion obtained by an operation.

Referring now to FIG. 4, in another preferred embodiment, the part to be treated is clamped in the work holder in step 400 while in step 402 a baseline distortion measurement is obtained for the untreated part to assess the viability of the treatment operation on that particular part. This measurement is compared to similar measurements for known parts. If the part, prior to treatment, contains unacceptable levels of distortion the process is stopped and the untreated part is discarded. Otherwise the process proceeds to step 404. In step 404, a treatment operation is performed. Following the treatment operation, in step 406, a distortion signature for the treated part is obtained and the total amount of distortion due to the operation is subsequently calculated in step 408. The propriety of this amount of distortion is then evaluated in step 410. In the next step, step 412, a decision point is reached based on the amount of distortion that has developed in the part. If the amount of distortion is in an acceptable range, the treatment is acceptable. If the distortion falls outside of the acceptable range, the process proceeds to step 414 where the signature is evaluated to determine if further treatment will yield an acceptable distortion.

Figure 5:
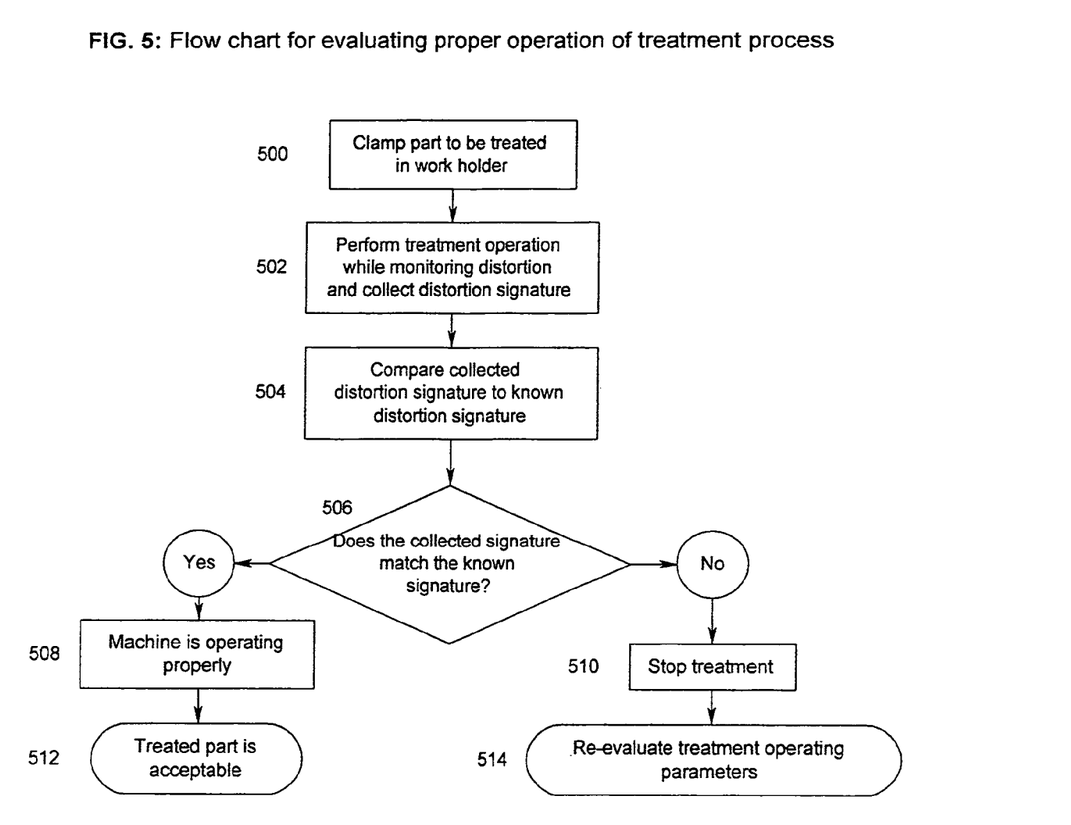
FIG. 5 is a flow diagram for evaluating the proper operation of machinery in a treatment operation.

Referring now to FIG. 5, in another preferred embodiment, the work holder is used to monitor the treatment equipment for faulty operation. In step 502, a distortion signature is collected for a particular operation while in step 504 this signature is compared to a known signature for a verified operation. The outcome of this comparison is passed to the decision point of step 510. Agreement between the two signatures causes the process to proceed to step 508, and a properly treated component is produced. Disagreement between the two signatures causes the process to proceed to step 510 at which point the process is terminated and the operating parameters of the machine are reassessed in step 514.

Figure 6:
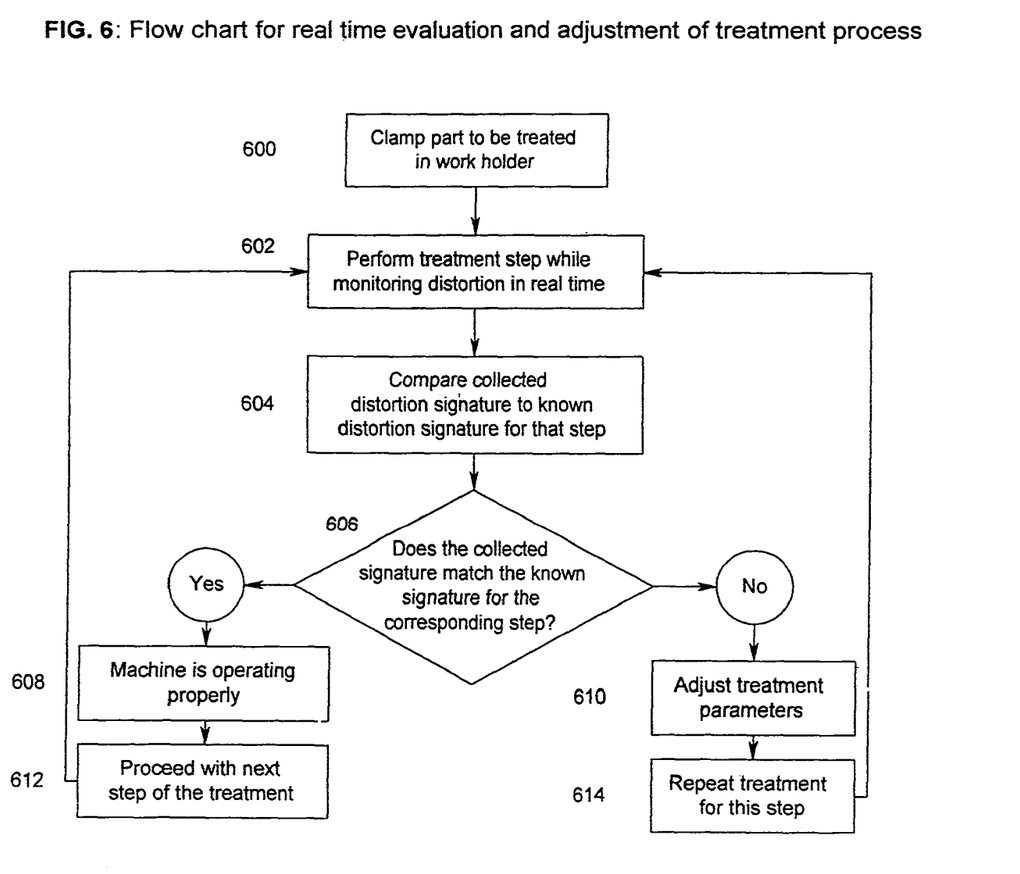
FIG. 6 is a flow diagram for the real-time evaluation and adjustment of a treatment process.

Referring now to FIG. 6, in another preferred embodiment of the current invention, the work holder is used to monitor individual steps of a treatment operation and thereby adjust treatment parameters to obtain the desired outcome of the operation. A part is secured in the work holder in step 600. In the next step, step 602, a distortion signature is collected for a given operation in the treatment process and subsequently compared to a known distortion signature for the same operation in step 604. If the signatures match, the process continues to step 612 and the next treatment operation is performed as the process is iterated. If the desired degree of agreement between the signatures is not found, the procedure continues to step 610 where the treatment parameters are adjusted. The same operation is then conducted on the part in step 614 and the evaluation of this treatment is again evaluated beginning with step 602.

Accordingly, the apparatus and method of the current invention provide a relatively inexpensive and effective system for monitoring the distortion in a part as a result of residual stresses induced in the part during treatment operations. By comparing the collected distortion signatures to known distortion signatures, it is not only possible to monitor the process for quality control purposes, but to also extrapolate the amount and location of residual stresses induced in the part based on the distortion that occurs.

While the method and apparatus described constitute preferred embodiments of the invention, it is to be understood that the invention is not limited to the precise method and apparatus, and that changes may be made therein without departing from the scope of the invention which is defined in the appended claims.

What is claimed is:

1. A method for evaluating the efficacy of a treatment operation for inducing residual stress along a surface of a part based upon the distortion developed in the part comprising the steps of:
    creating a verified distortion signature for a reference part having a desired amount of residual stresses induced in the part;
    coupling the part to be treated to a base effective for securing the part to be treated and attaching the base to an elastically deformable and recoverable material member such that any distortions developed in the part to be treated are communicated in real time to the material member and wherein the material member having strain or deflection sensing means for measuring distortion or strain along the material member;
        performing a treatment operation on the part to be treated to induce residual stresses along the surface of the part;
        measuring distortion or strain along the material member to create a collected distortion signature for the part being operated on;
        comparing the collected distortion signature to the verified distortion signature; and
        assessing if any deviations between the two signatures exist and, if so, whether those deviations are substantial enough to warrant discarding the treated part.

2. A method for evaluating the efficacy of a surface treatment operation conducted on a part based upon the distortion developed in the part comprising the steps of:
    clamping the part to be treated in a work holder having a base;
    attaching the part to be treated to a base and attaching the base to an elastically deformable an recoverable material member;
    acquiring a baseline signature for another part having a proper surface treatment operation performed on the part;
    performing a treatment operation on the part to be treated;
    determining the total amount of distortion occurring in the treated part as a result of the operation;
    communicating any distortions developed in the part during the treatment operation to the elastically deformable and recoverable material member to create a distortion signature;
    assessing whether the total amount of distortion that has developed in the treated part is within the established tolerances for the part;
    comparing the distortion signature to the baseline signature and assessing if any deviations between the two signatures exist and, if so, whether those deviations are substantial enough to warrant discarding the treated part.

3. A method for assessing the operation of equipment during a treatment process based on the distortion developed in a part comprising the steps of:
    clamping the part to be treated in a work holder;
    attaching the part to the work holder and attaching the work holder to an elastically deformable and recoverable material such that any distortions or stress developed in the part during the treatment process is communicated in real time to the elastically deformable and recoverable material;
    monitoring the distortion of or the strain developed in the elastically deformable and recoverable material and measuring the distortion or the strain to create a distortion signature while the part is treated;
    comparing, in real time, the distortion signature to a known and verified signature for another part that had a similar operation performed thereon;
    stopping the treatment should substantial deviations exist between the distortion signature and the known and verified signature;
    evaluating and adjusting the operational parameters based on the deviation from the known and verified signature; and
    reprocessing the treated part.

4. A method of monitoring and controlling a treatment operation based on the distortion developed in a part comprising the steps of:
    creating a verified distortion signature for each step of a successful treatment operation;
    clamping the part to be treated in a work holder;
    attaching the work holder to the part to be treated and attaching the work holder to a rigid, elastically deformable and recoverable material member such that the part to be treated is linked to the material member;
    performing a treatment step on the part to be treated while monitoring the distortion of the part in real time and create a distortion signature;
    measuring the strain developed in or the deflection of the material member during the treatment step;
    capturing and recording the strain in or the deflection of the material member;
    comparing the distortion signature with the verified distortion signatures for the same treatment step;
    adjusting control parameters based on deviations from the known, verified signatures;
    repeating the treatment step to obtain an acceptable distortion signature; and
    repeating the method for one or more additional treatment steps.

5. The method of claim 4 further includes the step of obtaining a baseline distortion measurement for the untreated part to assess the viability of the treatment operation for that part.

* * * * *